United States Patent [19]

Numata et al.

[11] Patent Number: 5,096,884
[45] Date of Patent: Mar. 17, 1992

[54] GLIDOBACTIN PF-1 PEPTIDE ANTIBIOTICS

[75] Inventors: Keiichi Numata, Fuchu; Masahisa Oka, Noba, both of Japan

[73] Assignee: Bristol-Myers Squibb Company, New York, N.Y.

[21] Appl. No.: 462,196

[22] Filed: Jan. 9, 1990

[51] Int. Cl.$^5$ .................................. C07K 5/12
[52] U.S. Cl. ........................... 514/11; 530/317
[58] Field of Search ..................... 530/317; 514/11

[56] References Cited

U.S. PATENT DOCUMENTS

| | | |
|---|---|---|
| 4,692,510 | 9/1987 | Konishi et al. |
| 4,742,047 | 5/1988 | Oka et al. |
| 4,777,160 | 10/1988 | Oka et al. ........................ 514/11 |
| 4,789,731 | 12/1988 | Oka et al. ........................ 530/317 |
| 4,833,076 | 5/1989 | Konishi et al. |

OTHER PUBLICATIONS

Numata, et al. *Journal of Antibiotics* 41 10, pp. 1358–1365.

Oka et al., *J. of Antibiotics*, vol. 41 (12), 1988, pp. 1812–1822.

*Primary Examiner*—Lester L. Lee
*Assistant Examiner*—A. Davenport
*Attorney, Agent, or Firm*—Mollie M. Yang; William T. Han

[57] ABSTRACT

Glidobactin PF-1 of the formula having antitumor activity is prepared by cultivation of *Polyangium brachysporum* in a nutient medium containing a suitable fatty acid ester, such linolenate, together with other assimilable sources of carbon and nitrogen.

2 Claims, 4 Drawing Sheets

GLIDOBACTIN PF-1 PEPTIDE ANTIBIOTICS

BACKGROUND OF THE INVENTION

1. Field of Invention

This invention relates to a novel peptide antibiotic and to its use as an antitumor agent. The present invention also relates to a method for the preparation of said antibiotic.

2. Description of the Prior Art

Two U.S. patents, U.S. Pat. No. 4,692,510 (Konishi, et al.), issued Sept. 8, 1987 and U.S. Pat. No. 4,777,160 (Oka, et al.), issued Oct. 11, 1988, disclose peptide antibiotics of formula I

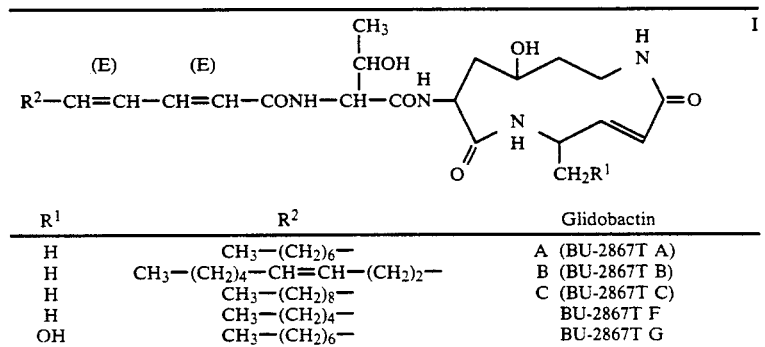

| $R^1$ | $R^2$ | Glidobactin |
|---|---|---|
| H | $CH_3-(CH_2)_6-$ | A (BU-2867T A) |
| H | $CH_3-(CH_2)_4-CH=CH-(CH_2)_2-$ | B (BU-2867T B) |
| H | $CH_3-(CH_2)_8-$ | C (BU-2867T C) |
| H | $CH_3-(CH_2)_4-$ | BU-2867T F |
| OH | $CH_3-(CH_2)_6-$ | BU-2867T G | which are produced by fermentation of *Polyangium brachysporum* sp. nov., strain K481-B101 (ATCC 53080). The above-mentioned peptide antibiotics were reported as having both antifungal and anti-tumor activities. In general, members of the series are referred to as glidobactins.

Other related art includes U.S. Pat. No. 4,789,731 (Oka, et al.), issued Dec. 6, 1988 and U.S. Pat. No. 4,742,047 (Oka, et al.), issued May 3, 1988, wherein semi-synthetic glidobactins also having anti-tumor properties are disclosed.

Another related art of the instant invention is disclosed in Numata, et al., *The Journal of Antibiotics*, 41, 10, pp. 1358-1365 (1988) and in U.S. Pat. No. 4,833,076 (Knoishi, et al.), issued May 23, 1989, wherein the authors report enriched production of glidobactins A, B, or C with the addition of certain fat or oil. Furthermore, enhanced production of glidobactins A, B, or C was also observed by precuring palmitoleate, linoleate, or oleate, respectively, to a production medium.

SUMMARY OF THE INVENTION

The present invention is concerned with a novel pepitide antibiotic, glidobactin PF-1, of formula II together with other assimilable sources of carbon and nitrogen under aerobic conditions and recovering the compound from the nutrient medium.

Testing in biological model systems showed that the compound of the present invention as having anti-tumor activity. Thus, a further aspect of the present invention is concerned with pharmaceutical compositions comprising an amount of formula II, effective as an antitumor agent, together with a pharmaceutically acceptable carrier.

DETAILED DESCRIPTION

Figure 1:
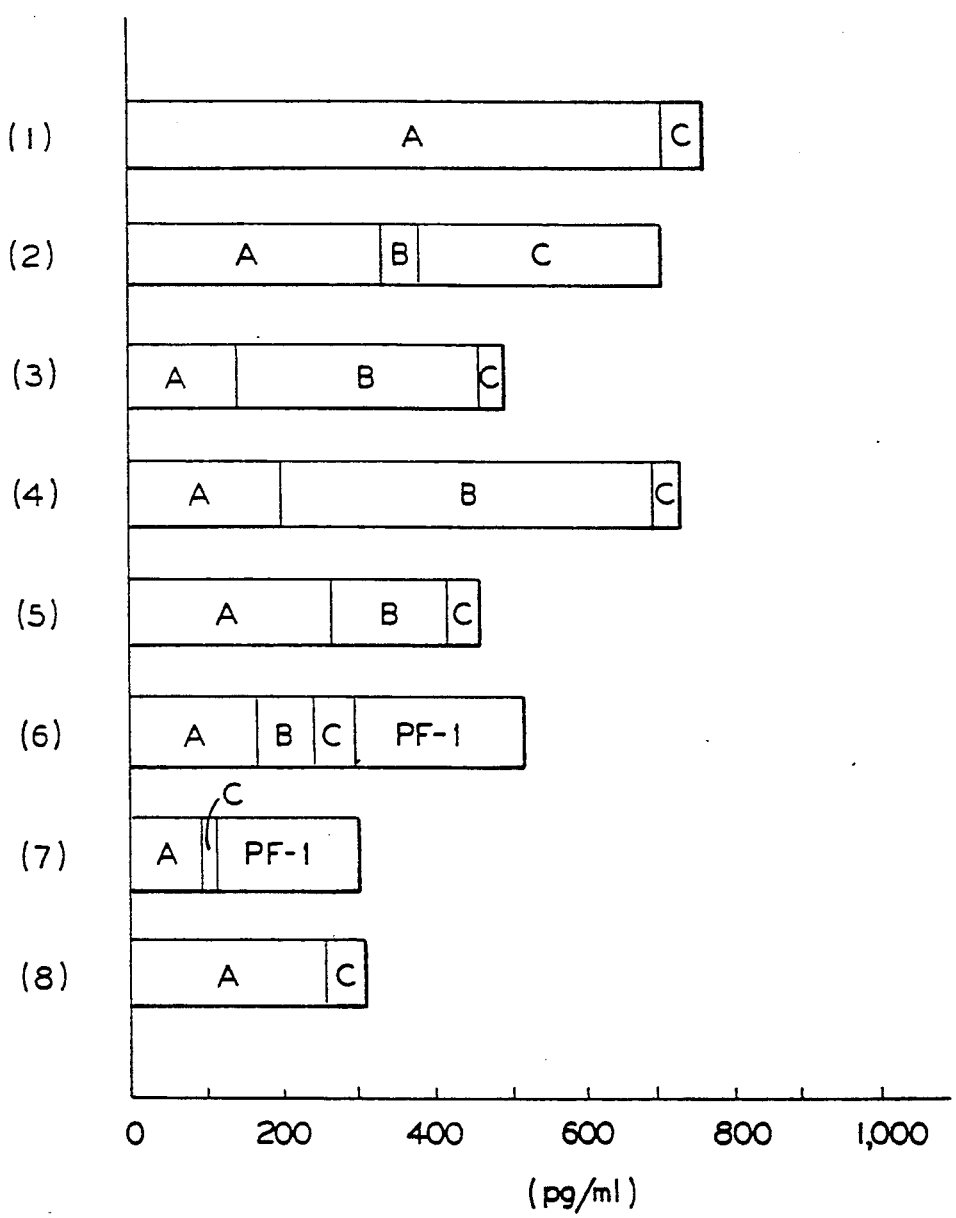
FIG. 1 is the effect of unsaturated fatty acids on the glidobactin production fed fermentation of *Polyangium brachysporum* sp. nov.

Glidobactin PF-1 may be produced by cultivating a glidobactin producing strain of *Polyangium brachysporum* having the characteristics of ATCC 53080 or a glidobactin PF-1 producing mutant thereof under submerged aerobic conditions in an aqueous nutrient medium. The organism is grown in a nutrient medium containing, together with other assimilable carbon source, a suitable fatty acid ester such as linolenate. Examples of preferred carbon sources are carbohydrates, which include lactose, glycerol, sucrose, corn starch, glucose, mannose and fructose. When starch is used as the carbon source in the nutrient medium, amylase may be added to the broth before harvest to reduce any emulsion problems which may occur. The nutrient medium should also contain an assimilable nitrogen source such as fish meal, peptone, soybean flour, peanut meal, cotton seed meal and corn steep liquor. Nutrient inorganic salts may also be incorporated in the medium

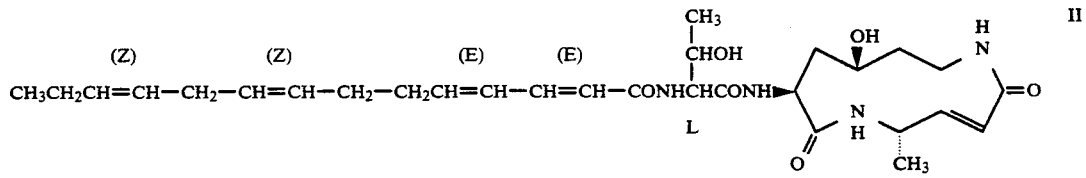

Another aspect of the present invention is concerned with a process for the preparation of the compound of formula II. Such a process comprises culturing *Polyangium brachysporum* sp. nov. in a nutrient medium containing a suitable fatty acid ester, such as linolenate, and such salts may comprise any of the usual salts capable of providing sodium, potassium, ammonium, calcium, phosphate, sulfate, chloride, bromide, nitrate, carbonate or like ions.

Production of glidobactin PF-1 antibiotic can be effected at any temperature conducive to a satisfactory growth of the organism, i.e. approximately 15° C.–42° C., and is conveniently carried out at a temperature of around 28° C. Ordinarily, optimum production is obtained after incubation periods of about 40 hrs in a 20-L fermentation vessel. The fermentation may be carried out in Erlenmeyer flasks and in laboratory or industrial fermenters of various capacities. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium for large scale production of the antibiotics. The medium in which the vegetative inoculum is produced can be the same as, or different from, that utilized in the tank for the production of the new antibiotic, as long as it is such that a good growth of the microorganism is obtained.

It is to be understood that for the production of glidobactin PF-1, the present invention, though described in detail with reference to the strain of *Polyangium brachysporum* K481-B101 (ATCC 53080), is not limited to said microorganism whose cultural characteristics were fully disclosed in five of our patents cited hereinabove. It is intended that this invention also includes other glidobactin PF-1 producing strains or mutants of the deposited microorganism which can be produced by methods well-known to those skilled in the art, e.g. by subjecting the deposited microorganism to X-ray or ultraviolet radiation, nitrogen mustard, phage exposure, or the like.

When the fermentation is complete, the antibiotic is extracted from the culture broth with a suitable organic solvent or a mixture thereof such as a mixture of n-butanol and methanol. The organic extract is concentrated, and the solid antibiotic complex is precipitated by dilution of the concentrated extract with a suitable antisolvent such as hexane.

Separation of the antibiotic from other antibiotics, such as from glidobactin A, B, and C and purification thereof may be carried out by conventional chromatographic procedures such as illustrated in the Description of Specific Embodiments which follows.

DESCRIPTION OF SPECIFIC EMBODIMENTS

Morphological, cultural, physiological, and taxonomical characterizations of K481-B101 are described in any of the five U.S. patents cited hereinabove.

CHEMICALS

Methyl esters of oleic acid, linoleic acid, and linolenic acid were purchased from Tokyo Chem. Ind. Co. Ltd. Methyl palmitoleate, methyl γ-linolenate, methyl 11, 14, 17-eicosatrieneate and methyl arachidonate were from Sigma Chem. Co. Ltd.

ANTIBIOTIC PRODUCTION

1. Media and Cultivation

The stock culture was maintained on a slant of the modified Bennett's agar medium composed of soluble starch 0.5%, glucose 0.5%, meat extract 0.1%, yeast extract 0.1%, NZ-case 0.2%, NaCl 0.2%, $CaCO_3$ 0.1% and agar 1.6% (pH 7.0). A well grown agar slant was used to inoculate a vegetative medium containing the same ingredients without agar as the above agar medium. After incubation at 28° C. for 48 hrs on a rotary shaker (200 rpm), an aliquot of the growth was transferred into a 500-mL Erlenmeyer flaskcontaining 100 mL of basal production medium FR-10-1. The medium is composed of soluble starch 2%, beet molasses 1%, soybean meal 1% and $CaCO_3$ 0.5% (pH 7.2, before autoclaving).

2. Determination of Glidobactin Productivity

The productivity of each component was determined by HPLC. The harvested broth (2 mL) was extracted by 3 mL of n-butanol with 15-min vigorous shaking and centrifuged for 10 min at 5,000 rpm. The solvent layer of the supernatant was applied to Waters QA-1 Analyzer with NOVA-PAK Radialpak cartridge. Aqueous methanol (70%) was used as a mobile phase at flow rate 1.0 mL/min, and the elution of each component was detected at 254 nm. The retention times for glidobactins PF-1, A, B, and C were 9.9, 10.8, 14.9, and 25.6 minutes, respectively.

3. Effect of Unsaturated Fatty Acids on Glidobactin Production

The fermentation with various unsaturated fatty acids was carried out using 50-mL Erlenmeyer flasks each containing 10 mL of the production medium. After shaking 8 hrs with 2% incoculum of vegetative culture, 100 μL of fatty acid was added to their flask. The incubation was continued on a rotary shaker for 7 days. The total production of glidobactins reached a maximum after 5 to 7 days. Addition of methyl esters of palmitoleate (C16:1), linoleate (C18:2), and oleate (C18:1) led to the increased production of naturally occurring glidobactins A, B, and C, respectively, without formation of any new artificial components. On the other hand, when methyl linolenate (C18:3) was supplemented to the production medium, HPLC analysis revealed the presence of a novel antibiotic, glidobactin PF-1.

Addition of α-linolenate led to the increased formation of glidobactin B. Although the addition of 1% methyl esters of eicosatrieneate (C20:3) or arachidonate (C20:4) to the fermentation broth inhibited the bacterial growth and glidobactin formation, the addition at lower concentration of eicosatrieneate or arachidonate led to the formation of glidobactin PF-1 or increased the formation of glidobactin B, respectively.

FIG. 1 shows the amount (μg/mL) of different glidobactin production on day 7 by feeding methyl esters of the following fatty acids:
(1) 1.0% Palmitoleate
(2) 1.0% Oleate
(3) 1.0% Linoleate
(4) 1.0% α-Linolenate
(5) 0.5% Arachidonate
(6) 1.0% Linolenate
(7) 0.5% Eicosatrienate
(8) no addition Our discovery that the addition of methyl linolenate caused the production of glidobactin PF-1 led us to examine the effect of linoleate concentration on the glidobactin production. As shown in Table 1, the optimal production of glidobactin PF-1 was observed when the concentration of linolenate was 1%.

4. Isolation and Purification of Glidobactin PF-1

Culture broth (9 L) was extracted with a mixture of n-butanol (9 ) and methanol (2.2 L). After being washed with water (2 L), the organic extract was concentrated to 200 mL of n-butanol solution. The resultant solution was added to n-hexane (1 L) with stirring to precipitate a crude active solid (8.2 g). The solid was dissolved in 70% aqueous methanol (100 mL) and was applied on a reverse phase silica gel column (1.2 L). Elution was performed with 60% (3.2 L), 70% (3.8 L), and 80% aqueous methanol (1.9 L), successively. The effluent was collected in fractions and monitored by a paper disk assay against *Candida albicans* A9540 and HPLC (column: SSC-ODS 262, Senshu Scientific Co; mobile phase, $CH_3OH:H_2O=4:1$; detection, UV 254 nm; retention times of glidobactins PF-1, A, B, and C: 4.9, 5.2, 6.6, and 10.2 minutes, respectively.) The first bio-active fractions containing glidobactin PF-1 were combined and evaporated to afford 1.97 g of a pale yellow solid. Work-up of the subsequent active fractions gave glidobactin A (970 mg), B (99 mg), and C (174 mg). The crude solid of glidobactin PF-1 (1.9 g) was rechromatographed on a same type of reverse-phase silica gel column (1.2 L) eluting with 60% (2.2 L) and then with 70% aqueous methanol (3.2 L). The eluate was monitored by the bioassay and HPLC. The appropriate fractions were combined and concentrated (1.22 g). A portion of the semi-pure solid (100 mg) obtained was further purified by preparative HPLC (column SSC-ODS 842 φ 3.0×25 cm, Senshu Scientific Co.; elution with 85% aqueous methanol, flow rate 7 mL/min; detection by UV absorption at 300 nm; retention time of glidobactin PF-1 at 30 min.) The relevant fractions were pooled, evaporated, and lyophilized to afford a pure white solid of glidobactin PF-1 (56 mg). Repetition of the above preparative HPLC purification for the remaining solid further afforded a total of 595 mg of glidobactin PF-1.

5. Physico-Chemical Properties and Sturctural Elucidation

Glidobactin PF-1 was isolated as a white amorphous powder. It was soluble in methanol, ethanol, n-butanol, and dimethyl sulfoxide but insoluble in n-hexane and water. The antibiotic gave a positive color reaction on TLC plate with Rydon-Smith reagent, iodine, and sulfuric acid. It was negative to ninhydrin, Sakaguchi, anthrone, and Dragendorff reaction. Secondary ion mass spectrometry (SI-MS) of glidobactin PF-1 gave the highest ion peak at m/z 545 $(M+H)^+$. This result, combined with microanalysis and $^{13}$C-NMR spectrum, indicated a molecular formula of $C_{29}H_{44}N_6$(MW 544) to glidobactin PF-1.

Figure 2:
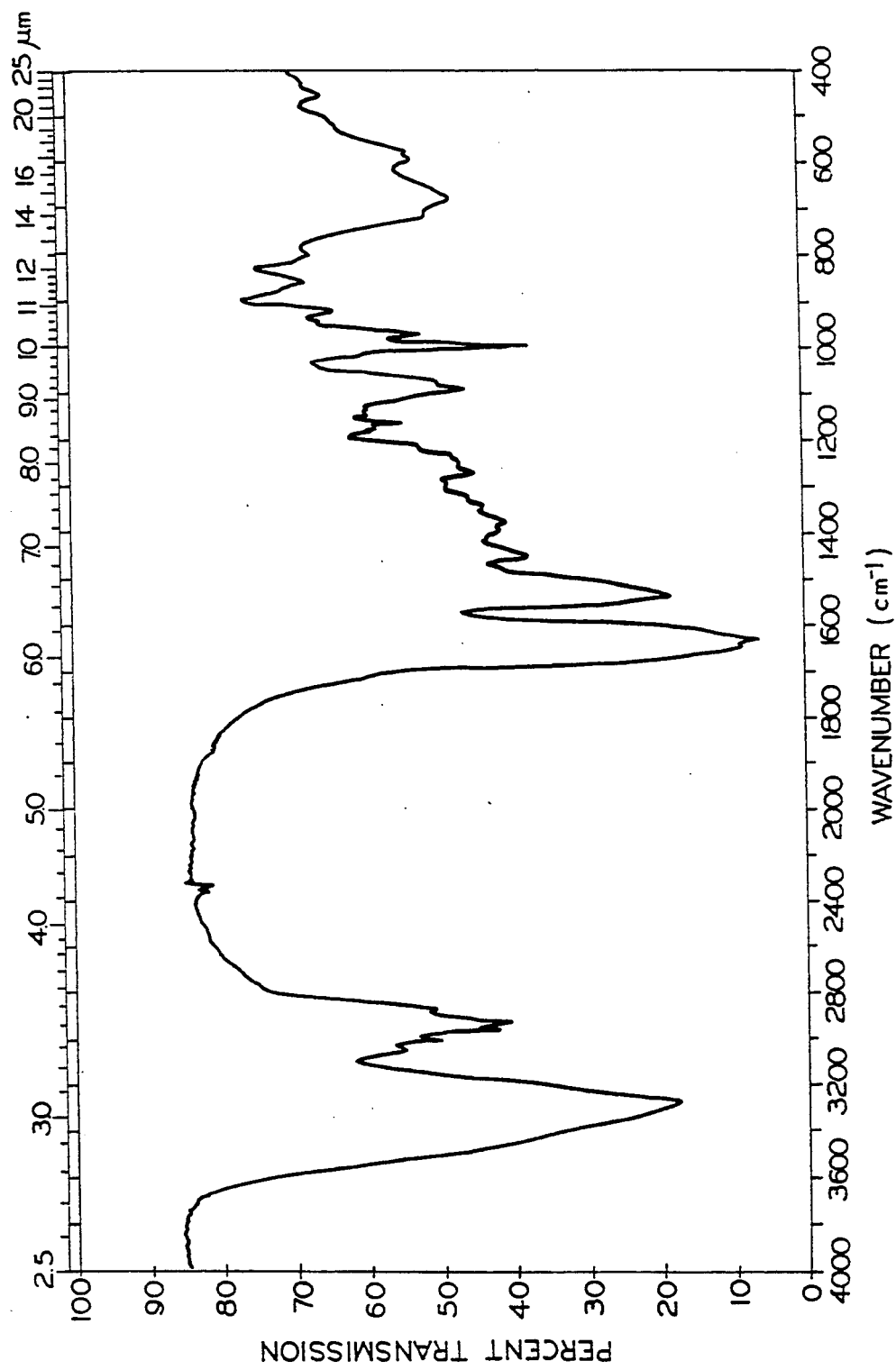
FIG. 2 is the IR spectrum of glidobactin PF-1.
Figure 3:
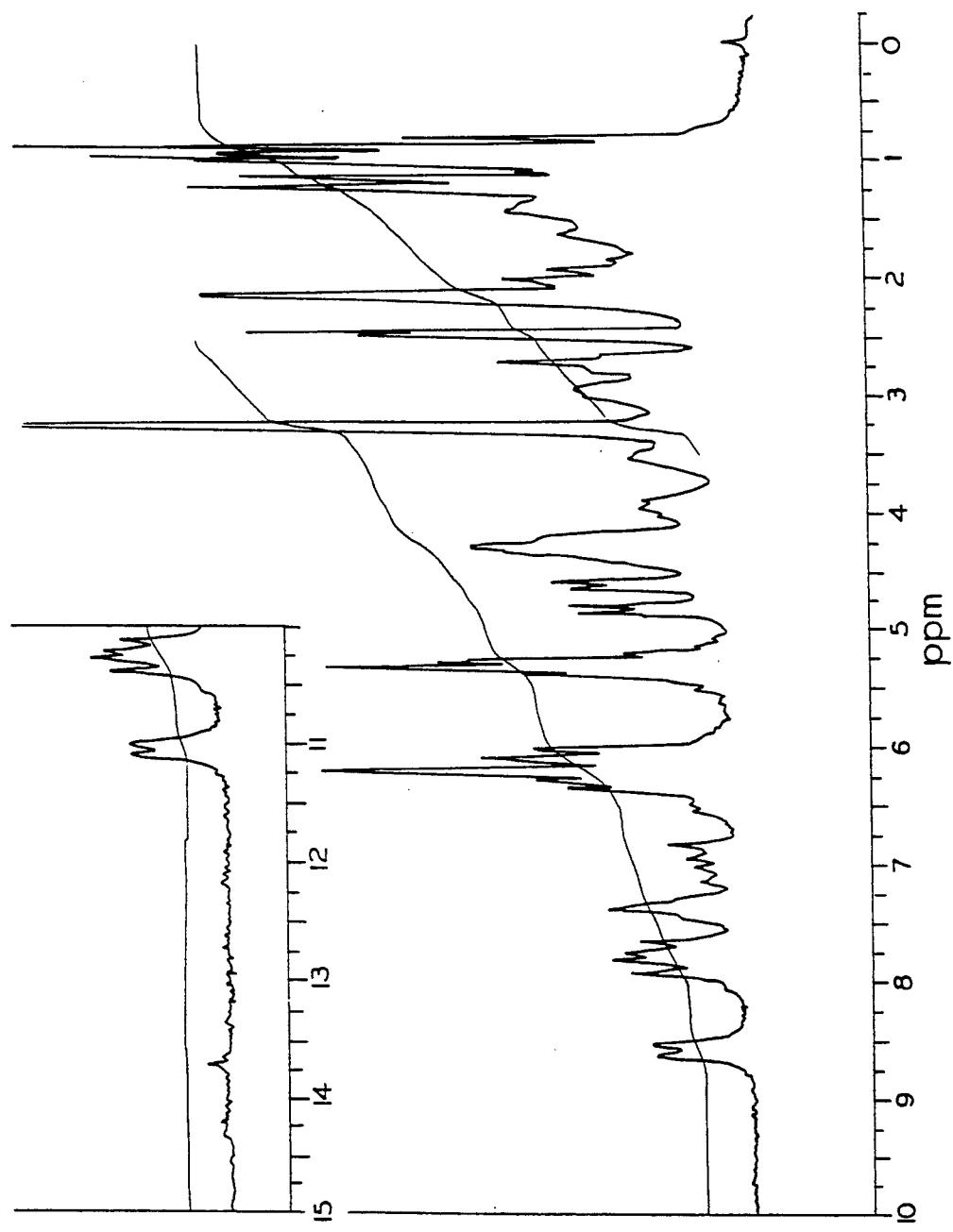
FIG. 3 is the NMR spectrum of glidobactin PF-1.
Figure 4:
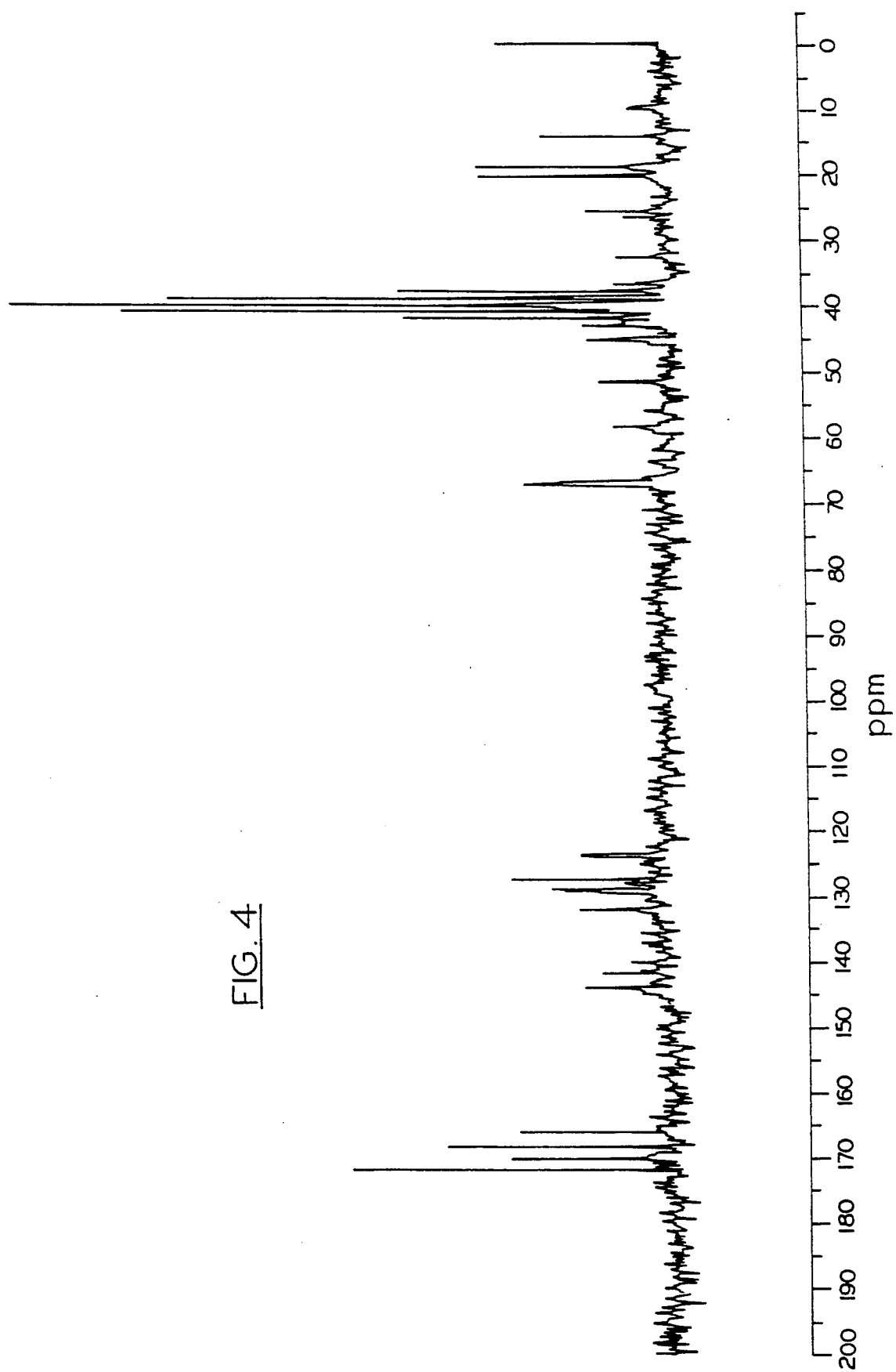
FIG. 4 is the $^{13}C$-NMR spectrum of glidobactin PF-1.

Physico-chemical properties of glidobactin PF-1 are summarized in Table 2. Its UV spectrum in methanol showed a strong absorption maximum at 261 nm. The IR spectrum (FIG. 2) indicated the presence of amide (1630 $cm^{-1}$ and 1530 $cm^{-1}$ and OH and/or NH (3300 $cm^{-1}$). The $^1$H-NMR spectrum (FIG. 3) revealed the presence of three methyls (δ: 0.92 ppm, t; 1.03 ppm, d; and 1.21 ppm, d), two hydroxyl protons (δ:4.65 ppm, d, and 4.86 ppm, d), ten olefinic protons (δ: 5.35 ppm, m, 4H; 6.2 ppm, m, 5H; and 6.98 ppm, dd, 1H), and four amide protons (δ: 7.38 ppm, t; 7.69 ppm, d; and 8.57 ppm, d). More than twenty-five carbon signals, including four carbonyl and ten olefinic carbon signals, were observed in the $^{13}$C-NMR spectrum (FIG. 4) of glidobactin PF-1. These data suggested that glidobactin PF-1 was structurally similar to glidobactins B and C, except for the degree of unsaturation. Thus, we determined that there are four double bonds in the fatty acid side chain of glidobactin PF-1. Two are conjugated to the carbonyl group and the other two are isolated.

The structure of glidobactin PF-1 was further determined by degradation experiments and spectral analyses in comparison to those of the glidobactins A, B, and C. Acid hydrolysis of glidobactin PF-1 with 6N HCl at 110° C. for 15 hrs in a sealed tube afforded the same amino acid complex, i.e., threonine, 4-amino-3-hydroxy-n-valeric acid, 4-amino-(2E)-pentenoic acid, and erythro-4-hydroxylysine, as that obtained from the naturally occurring glidobactins. Thus, the degradation experiments support that the differences among these antibiotics appear to reside only in the fatty acid portions.

The SI-MS spectrum of glidobactin PF-1 exhibited a protonated molecular ion peak at m/z 545 $(M+H)^+$, together with diagnostic fragment ion peaks at m/z 304 (tetradecatetraenoylthreonine) and m/z 242 (the cyclic amine) supporting a tetradecatetraenoyl side chain structure. The UV and $^1$H-NMR spectra demonstrated (2E, 4E)-dienoic acid structure possessing two other isolated double bonds in the acid chain. Its $^{13}$C-NMR spectrum was very similar to that of glidobactin B, except that the former contained two more $sp^2$ carbons (δ: 126.9–131.4) in place of two methylene carbons (δ: 28.3 and 30.5) of the latter.

The $^{13}$C-NMR signal shifts of the alkane by introduction of cis or trans double bonds are well-established [Wright, J. L. C., *Phytochemistry*, 19, pp. 143–144 (1980) and Rossi, et. al., *Tetrahedron*, 38, pp. 639–644 (1982).] We previously assigned the carbon NMR signals of the fatty acid (C6-C14) portion of glidobactin B as $CH_3$(δ: 13.4)—$CH_2$(21.5)—$CH_2$(30.5) —$CH_2$(28.3)—$CH_2$(25.6 or 26.3)—CH═CH(Z, 123.3 and 128.8)—$CH_2$(26.3 or 25.6)—$CH_2$(32.0)—based on the comparison made to those in gladobactin A. Furthermore, the additional isolated double bond in the fatty acid residue of glidobactin PF-1 of the present invention is now identified to reside at C11–C12 and to have the "Z" stereochemistry. In summary, the fatty acid residue of glidobactin PF-1 is (2E, 4E, 8Z, 11Z)-tetradecatetraenoic acid and the $^{13}$C-NMR signals are assigned as $CH_3$(δ:14.0)—$CH_2$(19.9)—CH═CH (Z,126.9–131.4)—$CH_2$(25.1)—CH═CH(Z126.9–131.4)—$CH_2$(27.0)—$CH_2$(32.0)—.

BIOLOGICAL ACTIVITY

1. Antimicrobial Activity

The minimum inhibitory concentrations (MIC's) of glidobactin PF-1 were determined for various microorganisms by a serial agar dilution method. Nutrient agar (Eiken) was used for bacteria and Sabouraud dextrose agar (Difco) for fungi. The inoculum size was adjusted to $10^4$ CFU/mL for bacteria and $10^5$–$10^7$ for fungi. Invitro antibacterial and antifungal activities of glidobactin PF-1 are shown in Table 3 together with the activities found with glidobactin C. Like other glidobactins, glidobactin PF-1 did not inhibit the bacteria tested at 100 μg/ml, but it showed moderate activity against fungi. The intrinsic antifungal activity of glidobactin PF-1 was considerably weaker than that of glidobactin C.

2. Antitumor Activity

Glidobactin PF-1 and glidobactin A were tested for in vitro cytotoxicity against murine tumor cell lines and for in vivo antitumor activity in mice. Mitomycin C was used as a reference compound in both in vitro and in vivo experiments. B16-F10 (murine melanoma) cells were grown to the logarithmic phase in an enriched Eagle minimum essential medium supplemented with fetal calf serum (FCS, 10%) and kanamycin (60 μg/ml). P388 (murine lymphocytic leukemia) cells were in RPMI1640 medium supplemented with FCS (10%), penicillin (100 U/ml), and streptomycin (100 μg/ml). B16-F10 and P388 cells were harvested and implanted into wells of a 96-well (for B16-F10 cells) and a 24-well (for P388 cells) tissue culture plate with test materials at the inoculum sizes of $3\times10^4$ and $2\times10^4$ cells/mL, respectively. They were incubated at 37° C. in a humidified atmosphere of 5% $CO_2$ and 95% air for 72 hrs. The cytotoxicity against B16-F10 cells was colorimetrically determined at 540 nm after staining viable cells with 0.006% neutral red solution. As for P388 cells, the number of viable cells was determined by a Coulter counter. As shown in Table 4, both glidobactins A and PF-1 exhibited potent cytotoxicity against B16-F10 and P388 cells.

Inhibitory effects of glidobactins A and PF-1 on macromolecule biosynthesis (DNA, RNA, and protein) were determined in cultured L1210 murine leukemia cells. The cells ($5\times10^5$ cells/mL) were incubated with test compounds at 37° C. for 15 min and further incubated for 4 hrs after the addition of labeled precursor, $^3H$-thymidine, $^{14}C$-uridine, or $^3H$-leucine into the cultured mixture. After washing with chilled 5% trichloroacetic acid solution, the radioactivity incorporated into the acid-insoluble fraction of the cells was determined by a liquid scintillation counter. As shown in Table 5, both glidobactins A and PF-1 inhibited protein synthesis. The inhibitory activity of glidobactin PF-1 was approximately half to that of glidobactin A. Both compounds showed no significant inhibitory effect on both DNA and RNA syntheses at 100 μg/mL, the highest concentration tested.

In vivo antitumor activity of glidobactin PF-1 was determined in experimental mouse tumor systems. Female $CDF_1$ and male $BDF_1$ mice were intraperitoneally inoculated with 0.4 mL of diluted ascitic fluid containing $10^6$ lymphocytic leukemia P388 cells and 0.5 mL of 10% melanotic melanoma B16 brei, respectively. Test compounds were intraperitoneally administered daily for 9 days starting from 1 day after the tumor implantation. Remarkably, as shown in Table 6, glidobactin PF-1 was approximately 4 times more potent than glidobactin A against P388. Both glidobactins A and PF-1 demonstrated relatively broad chemotherapeutic activity against P388 leukemia with maximum T/C values of 190% and 174%, respectively, whereas they showed no significant antitumor activity against ip-B16 melanoma at the doses tested.

It is apparent from the animal test results provided above that glidobactin PF-1 possesses effective inhibitory action against mammalian tumors. Accordingly, this invention provides a method for inhibiting mammalian tumors which comprises administering an effective tumor-inhibiting dose of the compound to a tumor bearing host.

The pharmacologically effective compound of this invention can be processed by conventional methods of galenic pharmacy into pharmaceutical preparation for oral or parenteral administration, e.g., to mammals including humans. Conventional excipients are pharmaceutically acceptable organic or inorganic carrier substance suitable for parental, enteral or topical application which do not deleteriously react with the active compound. Suitable pharmaceutically acceptable carriers include, but are not limited to water salt solutions, alcohols, gum arabic, vegetable oils, polyethylene glycols, gelatin, lactose amylose, magnesium stearate, talc, silicic acid, petrolatum, perfume oil, fatty acid monoglycerides and diglycerides, pentaerythritol fatty acid esters, hydroxy-methylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compound.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like; the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compound of this invention is dispensed in unit dosage form in a pharmaceutically acceptable carrier comprising the requisite dosage. The dosage of the compound according to this invention generally is 5–250 mg/day when administered to patients, e.g., humans weighing 75 kg. Suitable dosages and regimens for a given host can be determined using conventional considerations, e.g., by customary comparison of the differential activities of the subject compound and of a known antitumor agent, e.g., by means of an appropriate, conventional pharmacological protocol.

From the foregoing description, one skilled in the art can readily ascertain the essential characteristics of this invention, and without departing from the spirit and scope thereof, can make various changes and modifications of the invention to adapt it to various usages and conditions.

TABLE 1.

Effect of concentration of methyl linolenate on the production of glidobactin PF-1

| Concentration of methyl linolenate | Maximum* Day | Maximum* pH | Productivity (μg/ml) Total | Productivity (μg/ml) PF-1 | Composition (%) PF-1 | Composition (%) A | Composition (%) B | Composition (%) C |
|---|---|---|---|---|---|---|---|---|
| 0 (control) | 5 | 8.6 | 125 | 0 | 0 | 84 | 0 | 15 |
| 0.5% | 6 | 8.5 | 225 | 91 | 40 | 39 | 12 | 8 |
| 1.0% | 6 | 8.0 | 403 | 198 | 49 | 26 | 16 | 7 |
| 2.0% | 7 | 8.0 | 360 | 196 | 54 | 21 | 16 | 8 |
| 3.0% | 7 | 7.7 | 343 | 193 | 56 | 17 | 17 | 7 |

*The number represent the fermentation period and broth pH when the totally maximum production was observed.

TABLE 2.

Physico-chemical properties of glidobactin PF-1

| Nature | White powder |
|---|---|
| M.p. | 194–196° (dec.) |
| $[\alpha]_D^{24.5°}$ (C 0.25, MeOH) | −114° |
| Microanalysis Calcid for $C_{29}H_{44}N_4O_6 \cdot H_2O$ | |
| | C 61.90, H 8.24, N 9.96 |
| Found | C 61.84, H 8.17, N 9.62 |

TABLE 2.-continued

Physico-chemical properties of glidobactin PF-1

| | |
|---|---|
| SI-MS m/z | 545 (M + H)$^+$ |
| UV $\lambda_{max}^{MeOH}$ nm ($\epsilon$) | 261 (34,000) |
| TLC Silanized plate<br>EtOH—H$_2$O (55:45) | Rf 0.47 |
| HPLC SSC-ODS 262<br>MeOH—H$_2$(4:1)<br>Flow rate 1 ml/min | Rt 4.9' |

TABLE 5.

Inhibition of Macromolecule Synthesis in L1210 Leukemia Cells

| | IC$_{50}$ ($\mu$g/ml) | | |
|---|---|---|---|
| Compound | DNA | RNA | Protein |
| Glidobactin A | >100 | >100 | 0.03 |
| Glidobactin PF-1 | >100 | >100 | 0.07 |
| Mitomycin C | 1.7 | >100 | >100 |

TABLE 6.

Antitumor Activity Against P388 Leukemia (ip) and B16 Melanoma (ip)

| | T/C % of MST* Dose (mg/kg/day, ip, QD1→9) | | | | | | | |
|---|---|---|---|---|---|---|---|---|
| Compound | 2 | 1 | 0.5 | 0.25 | 0.13 | 0.063 | 0.031 | 0.016 |
| P388 Leukemia (ip—ip) | | | | | | | | |
| Glidobactin A | **Tox | 190 | 155 | 150 | 130 | 110 | 100 | — |
| Glidobactin PF-1 | **Tox | 130 | 174 | 170 | 160 | 133 | 129 | 118 |
| Mitomycin C | — | 225 | 190 | 170 | 145 | 140 | 115 | — |
| B16 Melanoma (ip—ip) | | | | | | | | |
| Glidobactin A | **Tox | 116 | 113 | 100 | 97 | — | — | — |
| Glidobactin PF-1 | **Tox | 111 | 113 | 118 | 103 | — | — | — |
| Mitomycin C | — | 200 | 166 | 134 | 100 | 100 | — | — |

*Ratio of MST (Median Survival Time) of test and control mice.
Values ≧ 125% indicate significant antitumor effect.
**Tox = Toxic

TABLE 3.

Antimicrobial Activity of Glidobactin PF-1

| | | MIC (mcg/ml) | |
|---|---|---|---|
| Test Organism | Medium* | Glidobactin PF-1 | Glidobactin C |
| Staphyloccocus aureus | 209P NA | >100 | >100 |
| Streptoccoccus faecalis | A9612 NA | >100 | >100 |
| Bacillus subtilis | PCI 219 NA | >100 | >100 |
| Escherichia coli | NIHJ NA | >100 | >100 |
| Klebsiella pneumoniae | D 11 NA | >100 | >100 |
| Pseudomonas aeruginosa | A9930 NA | >100 | >100 |
| Candida albicans | IAM 4888 SA | 12.5 | 0.4 |
| Candida albicans | A9540 SA | 6.3 | 0.2 |
| Cryptococcus neoformans | D49 SA | 25 | 0.8 |
| Aspergillus fumigatus | IAM 2530 SA | 12.5 | 1.6 |
| Fusarium moniliforme | A2284 SA | >50 | >50 |
| Piricularia oryzae | D9 SA | 12.5 | 6.3 |
| Trichophyton mentagrophytes | D155 SA | 12.5 | 0.8 |
| Blastomyces dermatitidis | IFO 8144 SA | 12.5 | 3.1 |
| Sporothrix schenckii | IFO 8158 SA | >50 | >50 |
| Mucor spinosus | IFO 5317 SA | 3.1 | 0.8 |

*Medium: NA(Nutrient agar), SA(Sabouraud dextrose agar).

TABLE 4.

In Vitro Cytotoxicities Against Murine Tumor Cells

| | IC$_{50}$ ($\mu$g/ml) | |
|---|---|---|
| Compound | B16-F10 | P388 |
| Glidobactin A | 0.04 | 0.008 |
| Glidobactin PF-1 | 0.07 | 0.010 |
| Mitomycin C | 0.50 | NT* |

*Not tested.

What is claimed is:

1. Glidobactin PF-1 having the formula $$\text{CH}_3\text{CH}_2\text{CH}\overset{(Z)}{=}\text{CH}-\text{CH}_2-\text{CH}\overset{(Z)}{=}\text{CH}-\text{CH}_2-\text{CH}_2\text{CH}\overset{(E)}{=}\text{CH}-$$

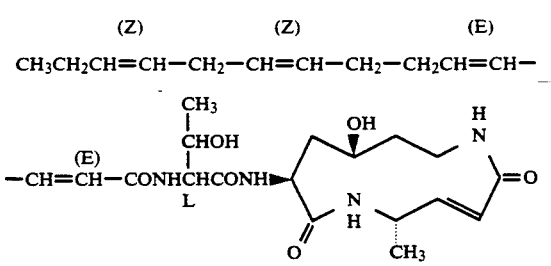

2. A pharmaceutical composition comprising as an active ingredient glidobactin Pf-1 associated with one or more pharmaceutically acceptable carriers, excipients or diluents therefor.

* * * * *